(12) United States Patent
Slage et al.

(10) Patent No.: US 7,349,947 B1
(45) Date of Patent: Mar. 25, 2008

(54) SYSTEM AND METHOD FOR MANAGING, MANIPULATING, AND ANALYZING DATA AND DEVICES OVER A DISTRIBUTED NETWORK

(75) Inventors: Irena Slage, Arlington, VA (US); Michael Slage, Arlington, VA (US); Hao Yu, Alexandria, VA (US)

(73) Assignee: Firelogic, Inc., Arlington, VA (US)

( * ) Notice: Subject to any disclaimer, the term of this patent is extended or adjusted under 35 U.S.C. 154(b) by 655 days.

(21) Appl. No.: 09/921,595

(22) Filed: Aug. 6, 2001

Related U.S. Application Data

(60) Provisional application No. 60/222,954, filed on Aug. 4, 2000.

(51) Int. Cl.
*G06F 15/16* (2006.01)

(52) U.S. Cl. ............................. 709/217; 707/10; 705/2

(58) Field of Classification Search ................ 709/217, 709/224; 705/2–3; 707/10, 104.1; 379/106.02; 600/301; 715/507; 704/2–3
See application file for complete search history.

(56) References Cited

U.S. PATENT DOCUMENTS

| | | | |
|---|---|---|---|
| 6,108,635 A * | 8/2000 | Herren et al. ................. 705/2 |
| 6,168,563 B1 * | 1/2001 | Brown ........................ 600/301 |
| 6,341,267 B1 * | 1/2002 | Taub ............................ 705/11 |
| 6,381,577 B1 * | 4/2002 | Brown ........................... 705/2 |
| 6,496,827 B2 * | 12/2002 | Kozam et al. ................ 707/10 |
| 6,602,469 B1 * | 8/2003 | Maus et al. ................ 422/68.1 |
| 6,611,846 B1 * | 8/2003 | Stoodley .................. 707/104.1 |
| 6,681,003 B2 * | 1/2004 | Linder et al. .......... 379/106.02 |
| 6,734,886 B1 * | 5/2004 | Hagan et al. ............... 715/853 |
| 6,789,091 B2 * | 9/2004 | Gogolak .................. 707/104.1 |
| 6,792,574 B1 * | 9/2004 | Sugiyama .................... 715/507 |
| 6,820,235 B1 * | 11/2004 | Bleicher et al. ......... 715/501.1 |
| 6,875,020 B2 * | 4/2005 | Niddrie et al. ............. 434/236 |
| 6,925,599 B2 * | 8/2005 | Wood ......................... 715/513 |
| 6,985,846 B1 * | 1/2006 | Dunlavey .................... 703/22 |
| 2001/0051882 A1 * | 12/2001 | Murphy et al. ................ 705/3 |
| 2002/0010595 A1 * | 1/2002 | Kapp ............................ 705/2 |

* cited by examiner

*Primary Examiner*—Salad Abdullahi
(74) *Attorney, Agent, or Firm*—Whitham Curtis Christofferson & Cook, P.C.

(57) ABSTRACT

A system and method for managing, manipulating, and analyzing data over a distributed network, such as the Internet is generally applicable to any field which could benefit from a centralized system for gathering, storing and analyzing data from multiple remote data sources over a distributed network. The present invention is particularly applicable for gathering, storing and analyzing health data from remotely located health data sources, such as remotely located medical devices, via the Internet.

10 Claims, 17 Drawing Sheets

SYSTEM AND METHOD FOR MANAGING, MANIPULATING, AND ANALYZING DATA AND DEVICES OVER A DISTRIBUTED NETWORK

CROSS-REFERENCE TO RELATED APPLICATIONS

This application claims the benefit of U.S. Provisional Application No. 60/222,954, filed Aug. 4, 2000. Application 60/222,954 is incorporated herein by reference in its entirety.

BACKGROUND OF THE INVENTION

This invention relates to systems and methods for collecting, managing, manipulating, visualizing, and analyzing data from data generating sensors and other devices over a distributed network. Such sensors, for the sake of generality, may be referred to as output devices (or data output devices), and may be thought of as including not just sensors, but also detectors, measuring devices, readers, identifiers, collectors, and the like. Likewise, the information that a particular device reads, measures, detects, identifies, collects, etc., may be thought of more generally as an observation of the device. More specifically, it describes a system and method for managing, manipulating, and analyzing such data and devices over a distributed network, such as the Internet.

The Internet has changed the way individuals address health concerns and manage well-being. Estimates are that the Internet today offers tens of thousands different healthcare sites, underscoring the large and growing consumer demand for access to health-related information, services, and products.

However, online health information service providers are struggling to satisfy the demand for personalized health information. They are constantly looking for applications that will make their offerings more attractive to end users. One such application is the ability to provide users with the means of keeping a personal health history online, which gave birth to the personal health record industry. We are already seeing online health diary/personal medical record and diet/fitness calendar applications haphazardly integrated across various health-oriented web sites and the number and variety are growing.

As the competition in the online health information space intensifies, companies are continuing to look for additional services, which could be of value to existing members and a "magnet" for bringing in new ones. At the same time, medical device manufacturers are already facing high levels of competition a variety of chronic disorder or wellness management fields, such as blood pressure monitoring, diabetes monitoring, asthma monitoring, and others. They are looking for differentiating features and functionality, with would enable them to compete effectively, reach more users, and command higher prices for existing products without making costly changes.

While enabling access to patient data locked in inaccessible medical devices is vital in being able to uncover long-term health trends, it is also important to be able to receive data pertaining to status and functionality of the device itself. Device-generated data, extrapolated over a large number of devices and analyzed in the appropriate manner, can give an insight into the weaknesses or trends in performance of the entire line of devices. When this information is unavailable, the decisions about the health of a particular line of devices has to be made over and extended period of time, which incurs additional costs, lapses in performance, and dissatisfaction of the users. When such information is available, it encourages further innovation as well as better and more reliable products for the end users.

SUMMARY OF THE INVENTION

In view of the above problems in the art, the present invention provides a system and method for managing, manipulating, and analyzing data over a distributed network, such as the Internet. The present invention is generally applicable to any field, which could benefit from a centralized system for gathering, storing and analyzing data from multiple remote data sources (especially data output devices) and delivering appropriate responses (including observation data) from and to such data sources via a distributed network. However, the present invention is particularly applicable for gathering, storing and analyzing health data from remotely located health data sources and delivering appropriate responses from and to data sources, such as remotely located medical devices and sensors (i.e., output devices), via the Internet.

The present invention can be achieved in whole or in part by a data engine that is configured to receive data from remotely located data sources via a distributed network. The data engine is configured to manage, manipulate, and analyze the data received from the remote data sources, as well as send data analysis results and pre-defined instructions to one or more data sources. The data engine is also configured to create pre-defined or user-defined graphical displays of the analyzed data (e.g., charts and graphs), and send the graphical displays to one or more data sources. The distributed network can be Internet-based or wireless.

The present invention can also be achieved in whole or in part by a server-based health data engine that is configured to receive health-related data from remotely located health data sources via the Internet or a wireless connection. The health data engine is configured to manage, manipulate, and analyze data received from the remote data sources, as well as send data analysis results and instructions to one or more data sources. The data engine is also configured to create pre-defined or user-defined graphical displays of the analyzed data (e.g., charts and graphs), and send the graphical displays to one or more data sources.

The present invention can also be achieved in whole or in part by a server-based data engine that is configured to receive data directly from remotely located devices or sensors via the Internet or a wireless connection. The data engine is configured to manage, manipulate, and analyze data received from the remote medical devices. The data engine is also configured to create user-defined graphical displays of the analyzed data (e.g., charts and graphs), and send the graphical displays to the remote devices or other defined data sources The accompanying drawings, which are incorporated in and constitute a part of this specification, illustrate the embodiments of the invention and, together with the description, serve to explain the principles of the invention.

BRIEF DESCRIPTION OF THE DRAWINGS

The preferred embodiments of this invention will be described in detail, with reference to the following figures, wherein.

DETAILED DESCRIPTION OF PREFERRED EMBODIMENTS

Figure 1:
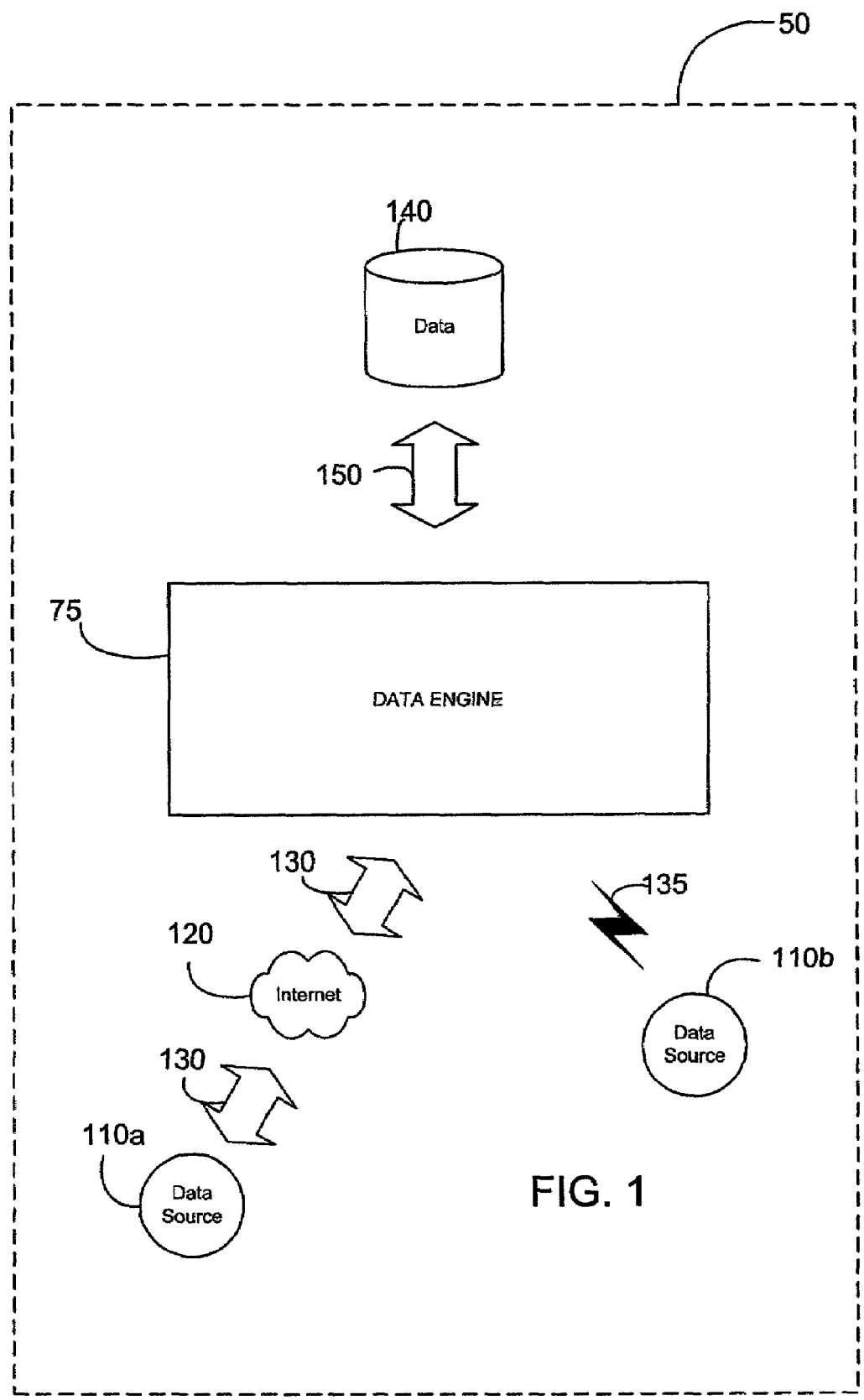
FIG. 1 is a block diagram of a system for managing, manipulating, and analyzing data from remotely located data sources, in accordance with the present invention.

FIG. 1 illustrates a system 50 for managing, manipulating, and analyzing data from remotely located data sources, in accordance with the present invention. The system 50 includes a data engine 75 and remotely located data sources 110a, 110b. The remotely located data sources 110a, 110b are configured to send data to the data engine 75 through a distributed network. For example, data source 110a sends data to the data engine 100 via the Internet 120 through communication links 130, and data source 110b sends data to the data engine 75 via a wireless network through a wireless communication link 135. The remotely located data sources 110a, 110b are suitably any source of data, such as medical devices or other types of precise measurement devices (i.e., data output devices). The data engine 75 is configured to manage, manipulate, and analyze data received from the data sources 110a, 110b, or from other sources. The data engine 75 is also configured to send results of data analysis back to the data sources 110a, 110b.

Figure 2:
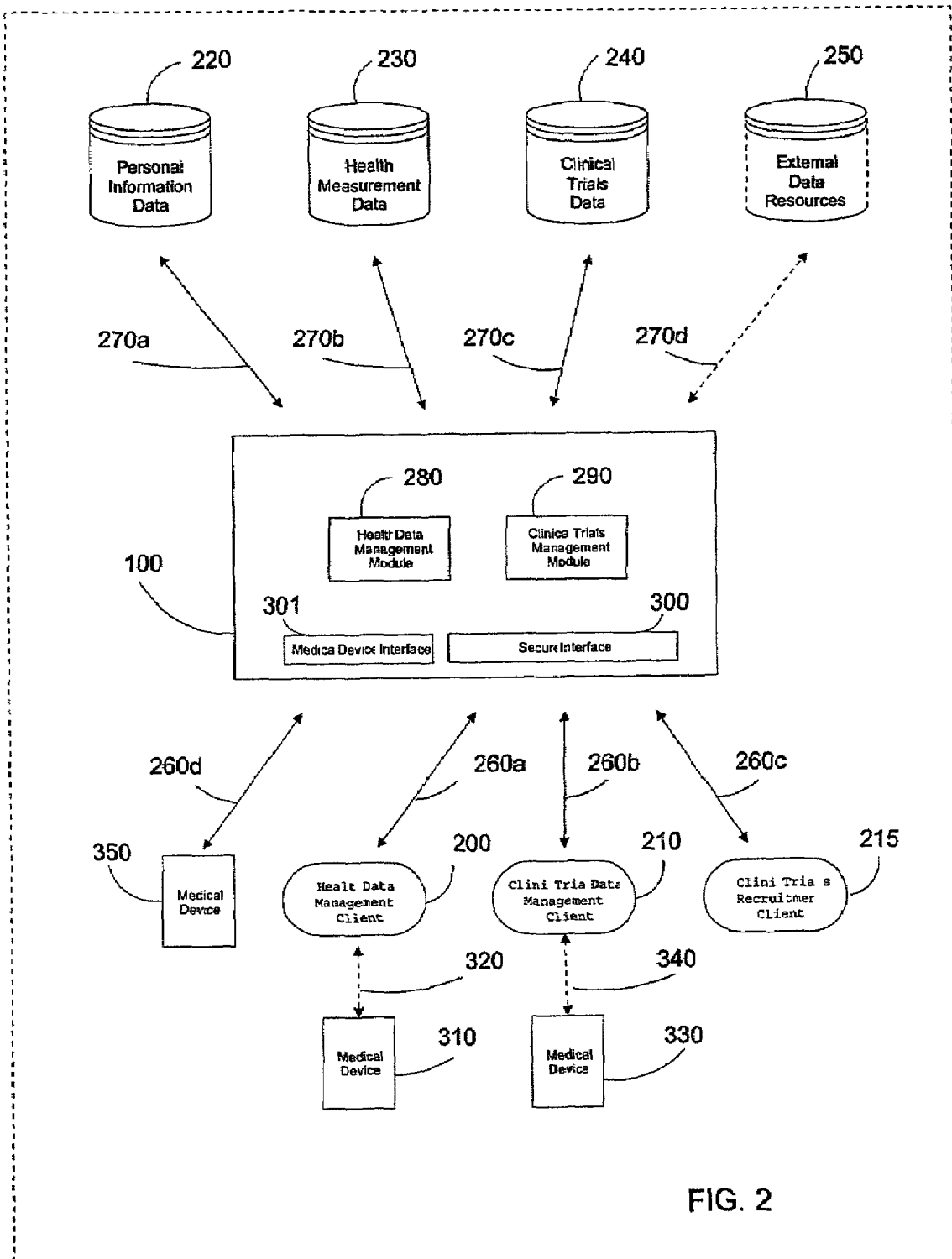
FIG. 2 is a schematic diagram of a system for managing, manipulating, and analyzing health data, in accordance with one embodiment of the present invention.

FIG. 2 is a schematic diagram of a system for managing, manipulating, and analyzing health data, in accordance with one embodiment of the present invention. The system comprises a health data engine 100, a health data management client 200, a clinical trials data management client 210, a clinical trials recruitment client 215, medical devices 310 and 330, a personal information database 220, a health measurement database 230, and a clinical trials database 240. The system may also make use of other external databases/resources 250.

The health data engine 100 preferably comprises a health data management module 280, a clinical trial management module 290, and a secure interface 300. The health data engine 100 communicates with the databases 220-250 via communication links 270a-270d, respectively. The health data management client 200, the clinical trials data management client 210 and the clinical trials recruitment client 215 communicate with the health data engine 100 via communication links 260a-260c, respectively.

In operation, the health data management client 200 receives data from medical device 310 and sends the data to the health data management module 280 via communication link 260a and secure interface 300. The health data management client 200 can be incorporated into the medical device 310 itself, or can be a stand-alone device that receives data from the medical device 310 via communication link 320. If the health data management client 200 is a stand-alone device, it is suitably a stand-alone device running a web browser-based application or as a stand-alone application.

If the health data management client 200 is a stand-alone device running a web browser-based client application, the web browser-based application is preferably a web browser plug-in that is a small, self-updateable application, and which functions inside a web browser window. If the health data management client 200 is stand-alone device running a stand-alone application, the stand-alone application is preferably installable using a self-guided installer program, preferably includes built-in driver libraries that allow for platform-independent connectivity, and preferably includes one-click interfaces for the entire process of secure login, data gathering and on-the-fly data charting.

The health data management module 280 comprises data analysis algorithms that are used to analyze the data from the medical device 310. The data analysis algorithms in the health data management module 280 can be customized for different types of data. For example, the health data management module 280 can include data analysis algorithms for analyzing cardiology data, diabetes data, allergy/immunology data, or any other type of health data. The health data management module 280 is preferably configured to send analyzed data back to the health data management client 200 via communication link 260a and secure interface 300. The analyzed data sent back to the health data management client 200 can be a simple on-demand data display, or more complex data charting, such as mathematical EKG pattern analysis and trend identification in large volumes of data. In prior art systems, such capabilities are limited to software bundled with high-end medical devices, and generally do not aggregate data over an extended period of time or from multiple data sources.

The analyzed data is also preferably sent to the health measurement database 230 via communication link 270b for storage. The personal information database 220 preferably stores encoded personal information for all users of the system in an ID-dependent manner. Whenever a request for analyzed health data is sent from the health data management client 200 to the health data engine 100, the health data management module 280 verifies that the user requesting the information is an authorized user by accessing the information from the personal information database 220. Once the user has been authenticated by the health data management module 280, the health data management module 280 retrieves the requested health data from the health measurement database 230 and sends the retrieved data to the health data management client 200.

The clinical trials data management client 210 and the clinical trials recruitment client 215 are also preferably implemented as a web browser-based client application or a stand-alone client application. The clinical trials recruitment client 215 is used by prospective clinical trial participants to enroll in a clinical trial. The clinical trial data management client 210 is used to manage data collected by the medical device 330 during a clinical trial. Both the clinical trials data management client 210 and the clinical trials recruitment client 215 communicate with the clinical trials management module 290 in the health data engine 100 via communication links 260*b* and 260*c*, respectively, and secure interface 300.

Similar to the health data management client 200, the clinical trials data management client 210 can be incorporated into the medical device 330 itself, or can be a stand-alone device that receives data from the medical device 330 via communication link 340.

Preferred control routines for the health data management client 200, clinical trials data management client 210, clinical trials recruitment client 215, health data management module 280 and clinical trials management module 290 will be discussed below.

Figure 3:
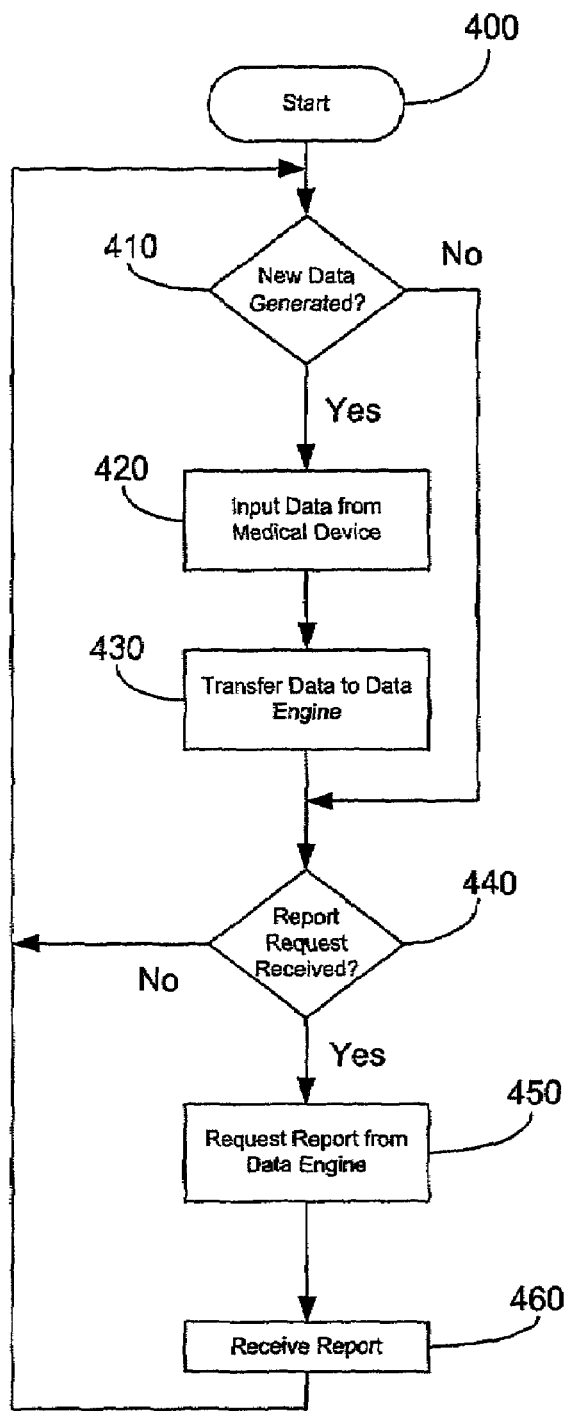
FIG. 3 is a flowchart of a preferred control routine for the health data management client of FIG. 2.

FIG. 3 is a flowchart of a preferred control routine for the health data management client 200 shown in FIG. 2. The routine starts at step 400 and proceeds to step 410, where the health data management client 200 determines if new data has been generated. If new data has been generated, control continues to step 420. Otherwise, control jumps to step 440.

At step 420, the data generated by the medical device 310 is input to the health data management client 200. Then, at step 430, the data is transferred to the health data engine 100 via network connection 260*a* and secure interface 300.

At step 440, the health data management client 200 determines if a report request has been received from the user. If a report request has been received, control continues to step 450. Otherwise, control returns to step 410.

At step 450, the health data management client 200 request a report from the health data engine 100. Next, at step 460, the health data management client 200 receives the requested report from the health data engine 100. Control then returns to step 410.

Figure 4:
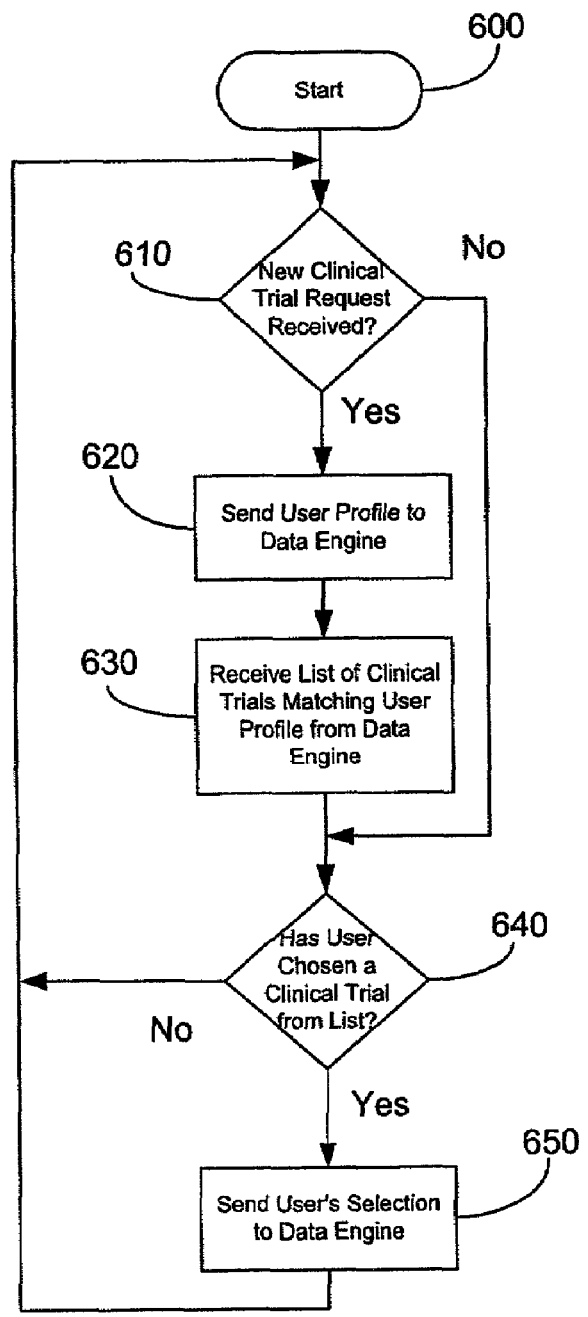
FIG. 4 is a flowchart of a preferred control routine for the clinical trials recruitment client of FIG. 2.

FIG. 4 is a flowchart of a preferred control routine for the clinical trials recruitment client 215 shown in FIG. 2. The routine starts at step 600, and proceeds to step 610, where the clinical trials recruitment client 215 determines if a new clinical trial request has been received from a user. If a new clinical trial request has been received, control continues to step 620. Otherwise, control jumps to step 640.

At step 620, the clinical trials recruitment client 215 sends the user's clinical trial profile to the health data engine 100. Next, at step 630, the clinical trials recruitment client 215 receives a list of clinical trials matching the user's profile from the health data engine 100.

Control then continues to step 640, where the clinical trials recruitment client 215 determines if a user has chosen a clinical trial from the list received from the health data engine 100. If the user has chosen a clinical trial, control continues to step 650. Otherwise, control returns to step 610. At step 650, the user's clinical trial selection is sent to the health data engine 100.

Figure 5:
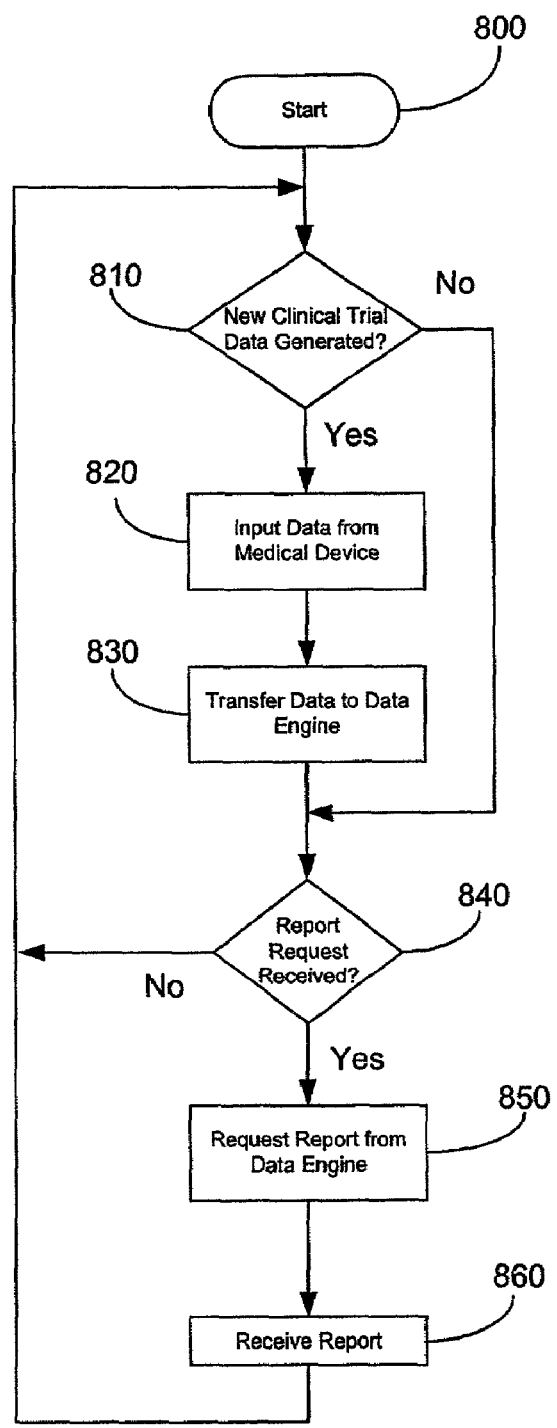
FIG. 5 is a flowchart of a preferred control routine for the clinical trial data management client of FIG. 2.

FIG. 5 is a flowchart of a preferred control routine for the clinical trial data management client 210 shown in FIG. 2. The routine starts at step 800 and continues to step 810, where the clinical trial data management client 210 determines if new clinical trial data has been generated by a medical device 330. If new clinical trial data has been generated, control continues to step 820. Otherwise control jumps to step 840.

At step 820, the clinical trial data management client 215 inputs the clinical trial data from the medical device 330. Next, at step 830, the clinical trial data is transferred to the health data engine 100.

At step 840, the clinical trial data management client 215 determines if a report request has been received from a user. If a report request has been received, control continues to step 850. Otherwise, control returns to step 810.

At step 850, the clinical trial data management client 215 requests a requested report from the health data engine 100. Then, at step 860, the clinical trial data management client 215 receives the requested report from the health data engine 100.

Figure 6:
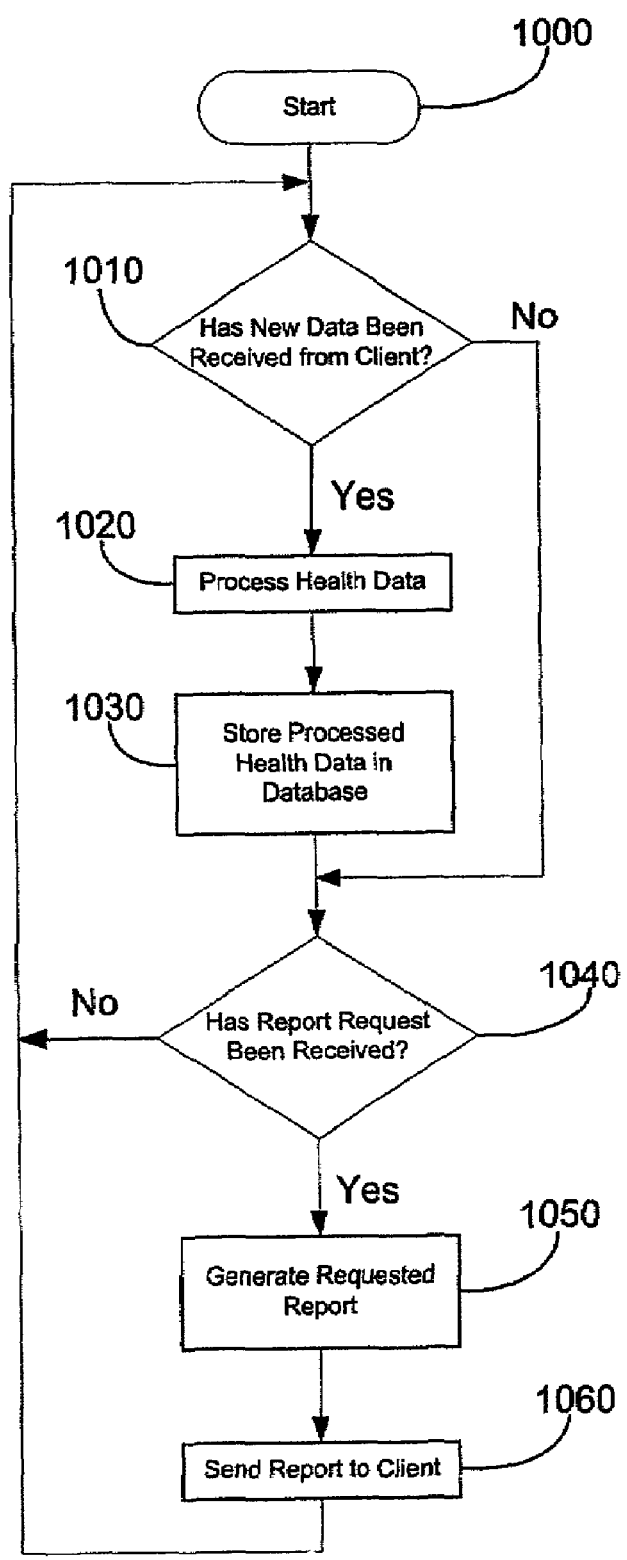
FIG. 6 is a flowchart of a preferred control routine for the health data management module of FIG. 2.

FIG. 6 is a flowchart of a preferred control routine for the health data management module 280 shown in FIG. 2 The routine starts at step 1000 and continues to step 1010, where the health data management module 280 determines if new data has been received from the health data management client 215. If new data has been received, control continues to step 1020. Otherwise, control jumps to step 1040.

At step 1020, the health data management module 280 processes the data received from the health data management client 200. Next, at step 230, the health data management module 280 stores the processed data in the health measurement database 230.

At step 1040, the health data management module 280 determines whether a report request has been received from the health data management client 200. If a report request has been received, control continues to step 1050. Otherwise, control returns to step 1010.

At step 1050, the health data management module 280 generates the requested report. Then, at step 1060, the generated report is sent to the health data management client 200. Control then returns to step 1010.

Figure 7:
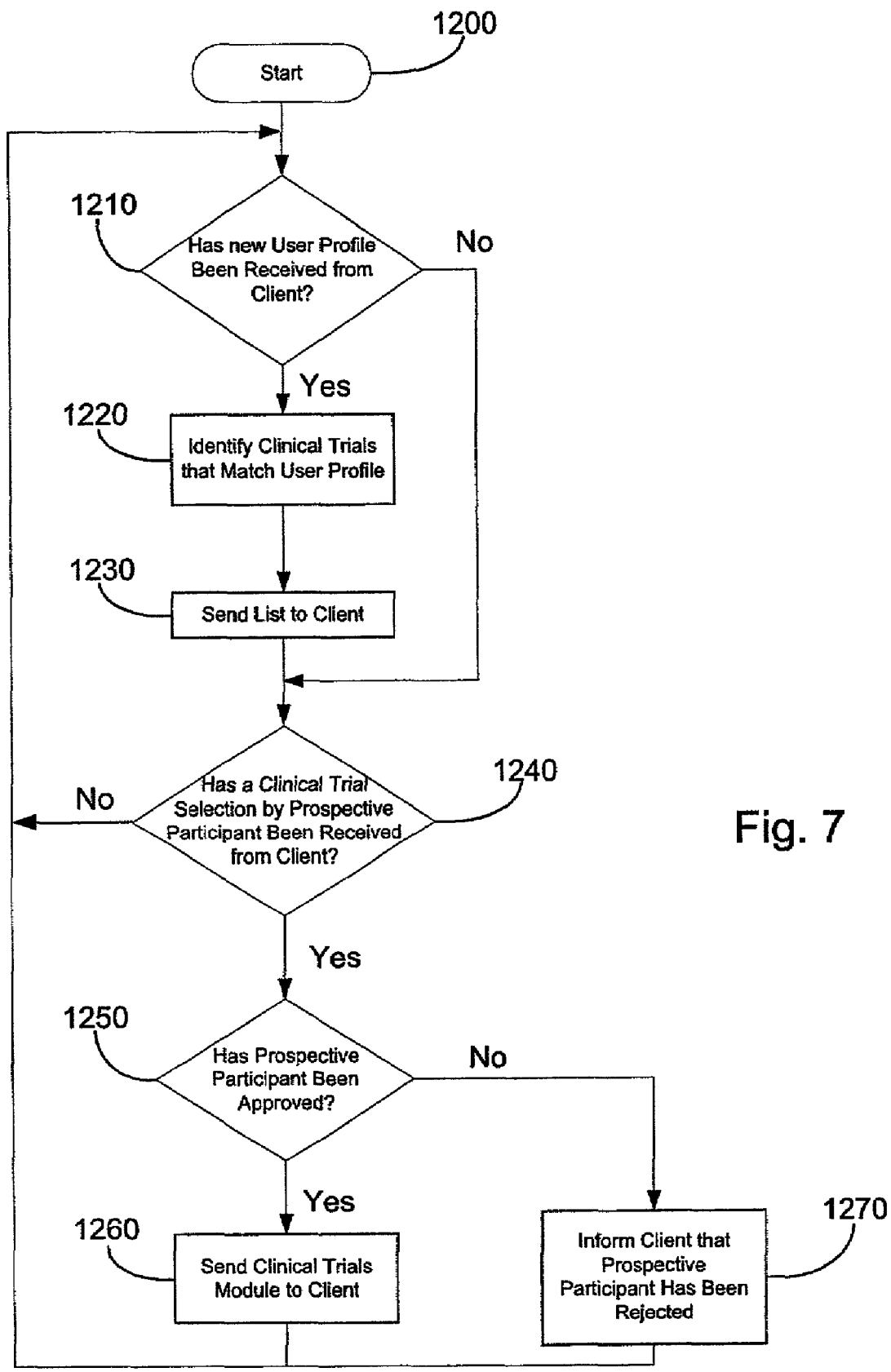
FIG. 7 is a flowchart of a preferred recruitment control routine used by the clinical trials management module of FIG. 2.

FIG. 7 is a flowchart of a preferred recruitment control routine used by the clinical trials management module 290 shown in FIG. 2. The routine starts at step 1200 and continues to step 1210, where the clinical trials management module 290 determines if a new user profile has been received from the clinical trials recruitment client 215. If a new user profile has been received, control continues to step 1220. Otherwise, control jumps to step 1240.

At step 1220, the clinical trials management module 290 identifies clinical trials that match the user profile sent by the clinical trials recruitment client 215. The clinical trials management module 290 does this by comparing the received user profile with clinical trials profiles already stored in the clinical trials database 240. Next, at step 1230, the clinical trials management module 290 sends a list of clinical trials that match the user profile to the clinical trial recruitment client 215.

Then, at step 1240, the clinical trials management module 290 determines if a clinical trial selection by a prospective participant has been received from the clinical trials recruitment client 215. If a clinical trial selection has been received, control continues to step 1250. Otherwise, control returns to step 1210.

At step 1250, the clinical trials management module 290 determines if the prospective participant has been approved. If the prospective participant has been approved, control continues to step 1260. Otherwise control jumps to step 1270.

At step 1260, the clinical trials management module 290 sends a clinical trials module to the clinical trials recruitment client 215 that will allow the approved participant to participate in the selected clinical trial. Control then returns to step 1210.

At step 1270, the clinical trials management module informs the clinical trial recruitment client 215 that the perspective participant has been rejected. Control then returns to step 1210.

Figure 8:
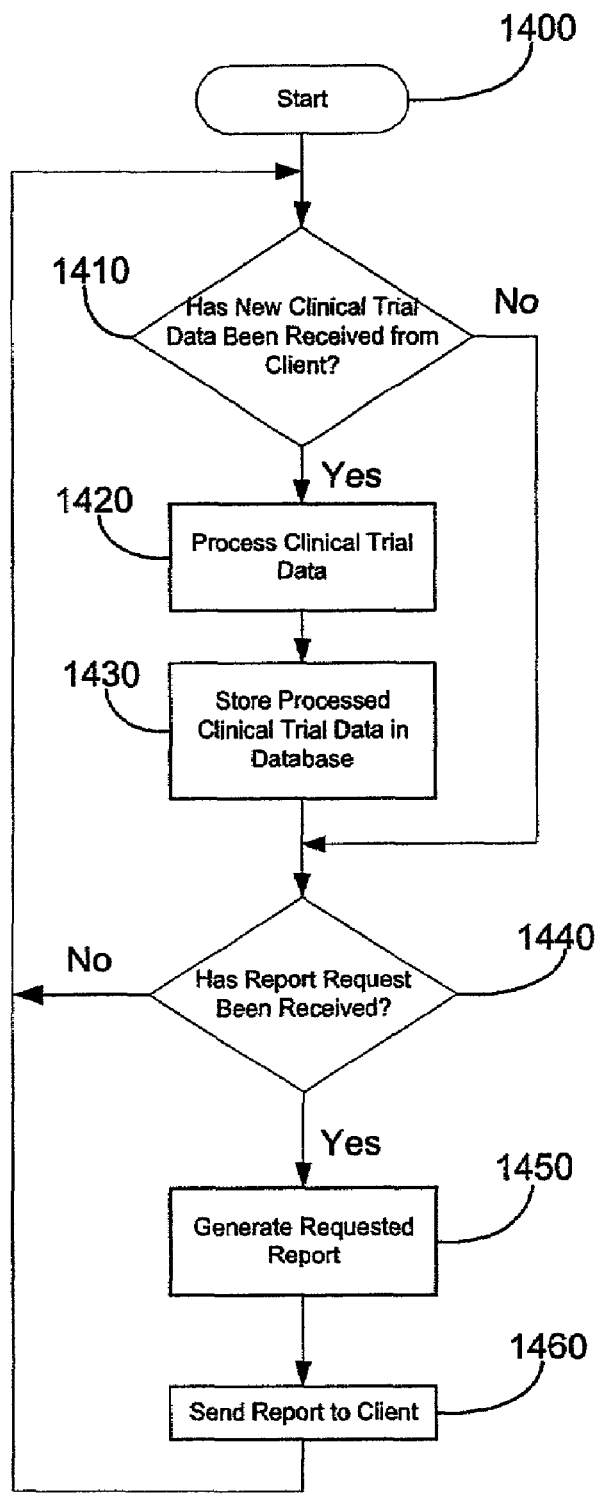
FIG. 8 is a flowchart of a preferred data management control routine used by the clinical trials management module of FIG. 2.

FIG. 8 is a flow chart of a preferred data management control routine used by the clinical trial management module 290 shown in FIG. 2. The routine starts at step 1400 and continues to step 1410, where the clinical trial management module 290 determines if new clinical trial data has been received from the clinical trials data management client 210. If new clinical trial data has been received, control continues to step 1420. Otherwise, control jumps to step 1440.

At step 1420, the clinical trials management module 290 processes the clinical trial data received from the clinical trials data management client 210. Next, at step 1430, the clinical trials management module 290 stores the processed clinical trial data in the clinical trials database 240.

At step 1440, the clinical trials management module 290 determines if a report request has been received from the clinical trials data management client 210. If a report request has been received, control continues to step 1450. Otherwise, control returns to step 1410.

At step 1450, the clinical trials management module 290 generates the requested report. Then, at step 1460, the clinical trials management module 290 sends the report to the clinical trials data management client 210. Control then returns to step 1410.

The data engine 75 and the health data engine 100 are preferably implemented with relational databases residing on secure servers. The servers may be or include, for instance, a workstation running the Microsoft Windows™ NT™, Windows™ 2000, Unix, Linux, Xenix, IBM AIX™, Hewlett-Packard UX™, Novell Netware™, Sun Microsystems Solaris™, OS/2™, BeOS™, Mach, Apache, OpenStep™ or other operating system or platform.

The health data management client 200, the clinical trials data management client 210 and the clinical trials recruitment client 215 may be or include, for instance, a personal computer running the Microsoft Windows™ 95, 98, Millenium™, NT™, or 2000, Windows™CE™, PalmOS™, Unix, Linux, Solaris™, OS/2™, BeOS™, MacOS™ or other operating system or platform. The health data management client 200, the clinical trials data management client 210 and the clinical trials recruitment client 215 may include a microprocessor such as an Intel x86-based device, a Motorola 68K or PowerPC™ device, a MIPS, Hewlett-Packard Precision™, or Digital Equipment Corp. Alpha™ RISC processor, a microcontroller or other general or special purpose device operating under programmed control.

The health data management client 200, the clinical trials data management client 210 and the clinical trials recruitment client 215 may furthermore include electronic memory such as RAM (random access memory) or EPROM (electronically programmable read only memory), storage such as a hard drive, CDROM or rewritable CDROM or other magnetic, optical or other media, and other associated components connected over an electronic bus, as will be appreciated by persons skilled in the art.

The health data management client 200, the clinical trials data management client 210 and the clinical trials recruitment client 215 may also be or include a network-enabled appliance such as a WebTV™ unit, radio-enabled Palm™ Pilot or similar unit, a set-top box, a networkable game-playing console such as Sony Playstation™ or Sega Dreamcast™, a browser-equipped cellular telephone, or other TCP/IP client or other device.

The communication links 130, 135, 150, 260a-260c, 270a-270d, 320 and 340 may be, include or interface to any one or more of, for instance, the Internet, an intranet, a PAN (Personal Area Network), a LAN (Local Area Network), a WAN (Wide Area Network) or a MAN (Metropolitan Area Network), a storage area network (SAN), a frame relay connection, an Advanced Intelligent Network (AIN) connection, a synchronous optical network (SONET) connection, a digital T1, T3, E1 or E3 line, Digital Data Service (DDS) connection, DSL (Digital Subscriber Line) connection, an Ethernet connection, an ISDN (Integrated Services Digital Network) line, a dial-up port such as a V.90, V.34 or V.34bis analog modem connection, a cable modem, an ATM (Asynchronous Transfer Mode) connection, or an FDDI (Fiber Distributed Data Interface) or CDDI (Copper Distributed Data Interface) connection.

The communication links 130, 135, 150, 260a-260c, 270a-270d, 320 and 340 may furthermore be, include or interface to any one or more of a WAP (Wireless Application Protocol) link, a GPRS (General Packet Radio Service) link, a GSM (Global System for Mobile Communication) link, a CDMA (Code Division Multiple Access) or TDMA (Time Division Multiple Access) link such as a cellular phone channel, a GPS (Global Positioning System) link, CDPD (cellular digital packet data), a RIM (Research in Motion, Limited) duplex paging type device, a Bluetooth radio link, or an IEEE 802.11-based radio frequency link.

The communication links 130, 135, 150, 260a-260c, 270a-270d, 320 and 340 may yet further be, include or interface to any one or more of an RS-232 serial connection, an IEEE-1394 (Firewire) connection, a Fibre Channel connection, an IrDA (infrared) port, a SCSI (Small Computer Systems Interface) connection, a USB (Universal Serial Bus) connection or other wired or wireless, digital or analog interface or connection.

The databases 220, 230, 240 and 250 may be, include or interface to, for example, the Oracle™ relational database sold commercially by Oracle Corp. Other databases, such as Informix™, DB2 (Database 2), Sybase or other data storage or query formats, platforms or resources such as OLAP (On Line Analytical Processing), SQL (Standard Query Language), a storage area network (SAN), Microsoft Access™ or others may also be used, incorporated or accessed in the invention.

Figure 9:
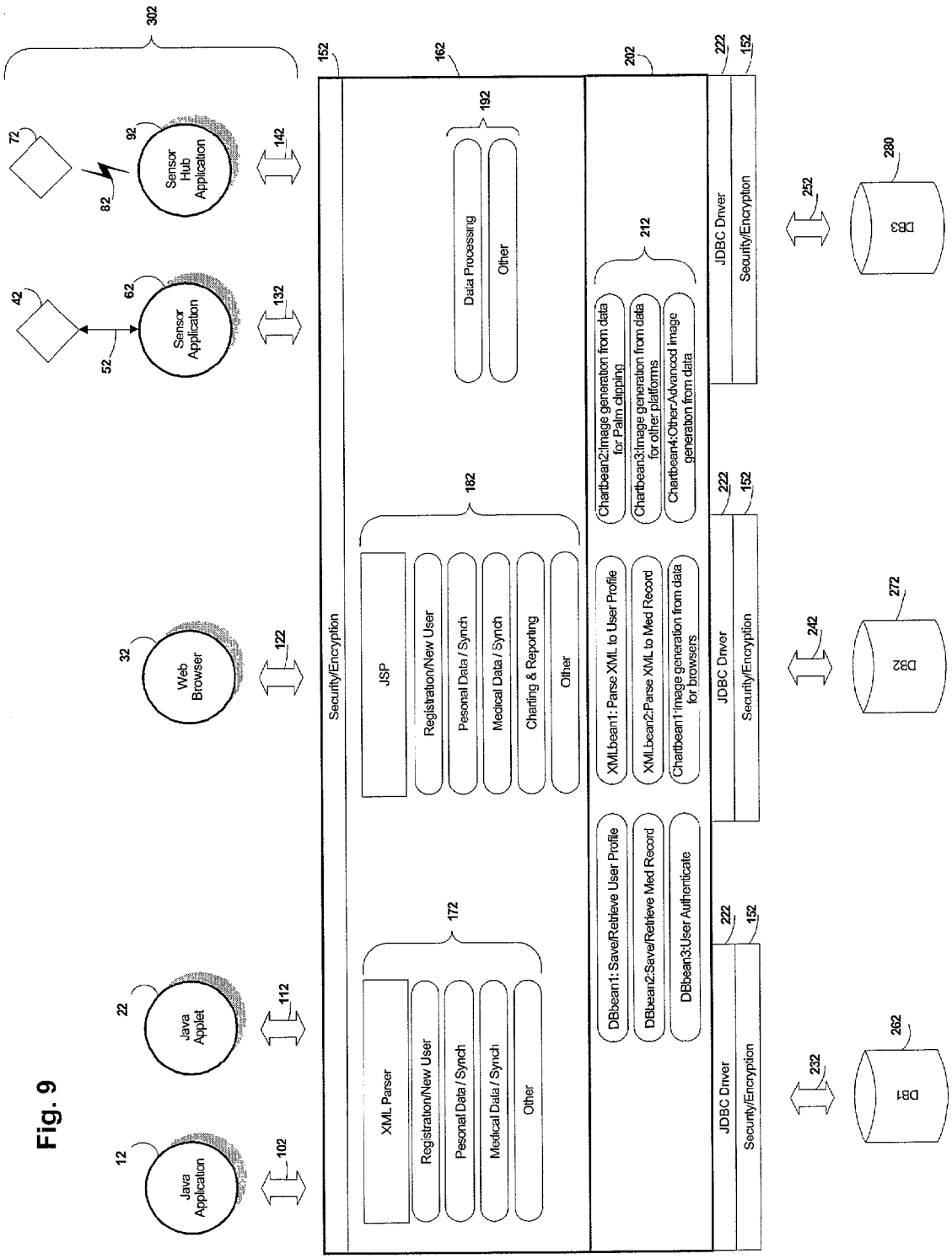
FIG. 9 is a simplified schematic diagram showing a preferred manner of implementing the data engine at a server in a health care related implementation.

The discussion of the preferred embodiments will now continue with reference to FIG. 9, in which a preferred implementation of the engine is illustrated in a highly simplified diagrammatic fashion.

In FIG. 9, 302 indicates some of the different ways in which interaction with the engine may be performed. Reference 12 indicates a Java application communicating with the server via a communication link 102. Reference 22 indicates a Java applet communicating via communication link 112. Reference 32 indicates a Web browser interacting via the communication link 122. Medical devices 42 and 72 communicate with the engine by way of links or connections 52 and 82 with sensor applications 62 and 92, respectively, and via communication links 132 and 142, respectively. It will be understood that the client's 12 and 22 are Java applications and applets, and hence more of the processing occurs at the client than is the case with Web browser 32, in which substantially all of the processing must occur at the server.

At the server, there is a security layer 152. This layer is well understood by those familiar with this field, and further description thereof will be omitted for the sake of clarity. Reference 162 indicates servlets running on the server. The servlets 172 are those necessary to handle the processing at the server for the Java application 12 and the Java applet 22. The servlets 182 are those necessary to handle the processing at the server for clients that access the system via the Web browser 32. The servlets 192 are configured as necessary to support and to interact with the sensor applications 62 and 92.

Reference 202 indicates some of the JavaBeans 212 for interacting with databases, performing image generation, parsing XML, authenticating users, and the like. As will be familiar to those experienced in this field, 222 indicates the JDBC driver, and 152 again indicates a security layer. For the sake of illustration, there are shown three databases (262, 272, and 280) with which this particular implementation of the engine is shown interacting via respective communication links 232, 242, and 252.

It will be appreciated that the many specificities is shown in FIG. 9 are for the sake of showing only one way among the many different ways of realizing an embodiment of the invention in a practical manner.

The discussion of the preferred embodiments will now continue with reference to FIGS. 10-15, in which a preferred implementation of the client is illustrated. The client may be described in terms of a user interface. Thus, the invention is also embodied in a user interface invocable by an application program. A user interface may be understood to mean any hardware, software, or combination of hardware and software that allows a user to interact with a computer system. For the purposes of this discussion, a user interface may be understood to include one or more user interface objects. User interface objects may include display regions, activatable regions, and the like.

As is well understood, a display region is a region of a user interface which displays information to the user. A user activatable region is a region of a user interface, such as a button or a menu, which allows the user to take some action with respect to the user interface.

A user interface may be invoked by an application program. When an application program invokes a user interface, it is typically for the purpose of interacting with a user. It is not necessary, however, for the purposes of this invention, that an actual user ever interact with the user interface. It is also not necessary, for the purposes of this invention, that the interaction with the user interface be performed by an actual user. That is to say, it is foreseen that the user interface may have interaction with another program, such as a program created using macro programming language statements that simulate the actions of a user with respect to the user interface.

Figure 10:
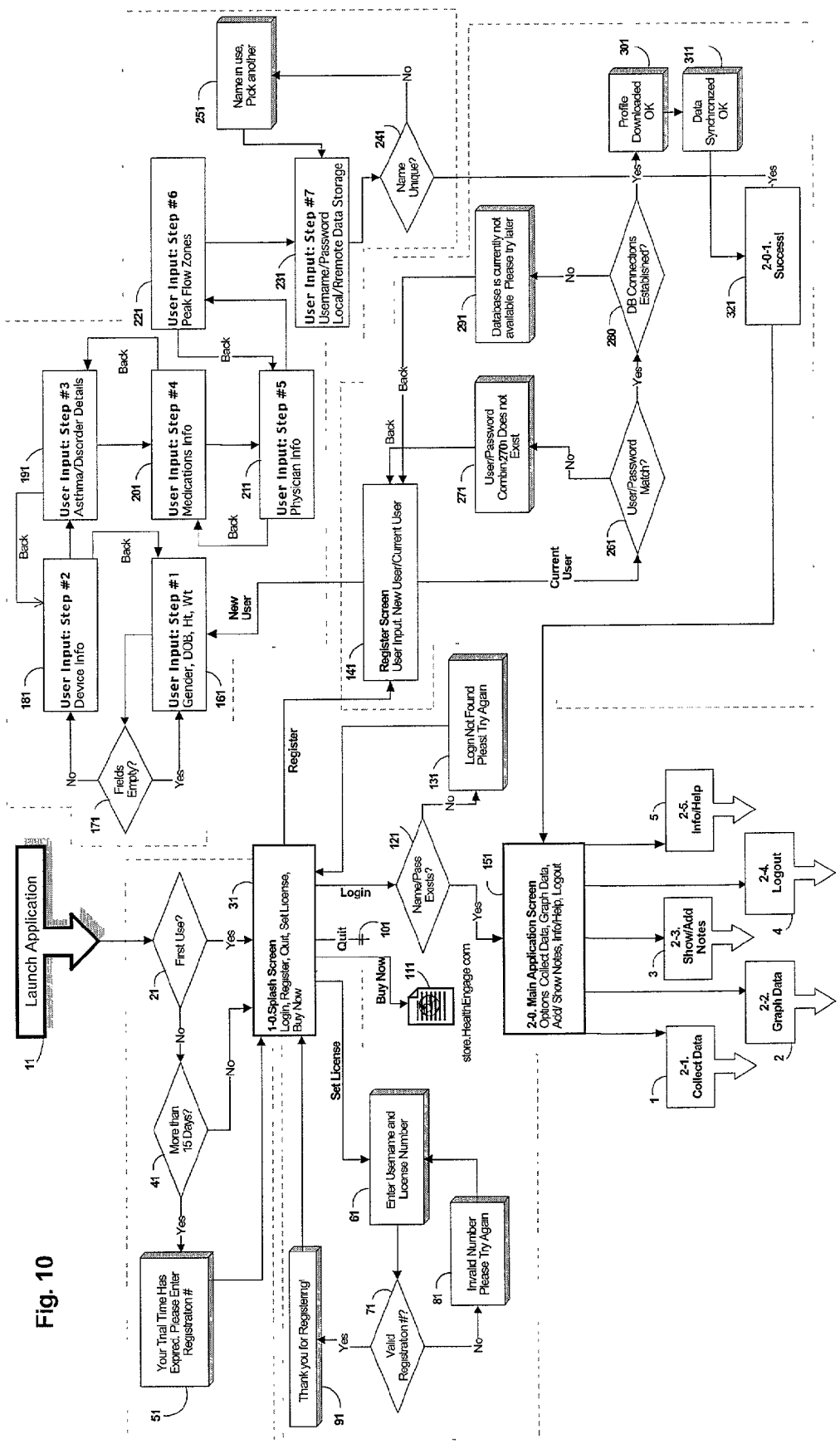
FIG. 10 is a schematic diagram showing a preferred manner of implementing a client according to one embodiment of the invention.

In FIG. 10, reference 11 indicates a step of launching the application at the client. At step 21, it is determined whether the application has been previously used. If the current use is the first use, then processing continuous with a display of a "splash screen" at which the user is invited to login, to register, to quit, to enter a license number, or to purchase such a license (see reference 31). If the present use is not the first use, then processing continuous with step 41, in which it is determined whether it has been more than 15 days since the beginning of a free trial period for using the software. If yes, then processing continuous with step 51 at which the user is invited to enter a registration number. If not, then processing continuous with the splash screen 31. Assuming that the user enters the registration number in step 51, then processing also continuous with the splash screen 31.

From this screen, registration may be effected by steps 141, 261, 271, 281, 291, 301, 311, and 321 in a manner which will be readily understood by one familiar with this field. Also from the splash screen 31, the license information can be entered as shown in steps 61, 81, 71, and 91. Similarly, a purchase operation 111, a quit operation 101, and a login operation (121 and 131) may be performed from the splash screen 31.

After successful login or registration, processing continues with the main application screen 151. From the main application screen, the principal functions include data collection (reference 1—FIG. 11), data graphing (reference 2—FIG. 12), show/add notes (reference 3—FIG. 13), logging out (reference 4—FIG. 14), and obtaining help (reference 5—FIG. 15).

Figure 11:
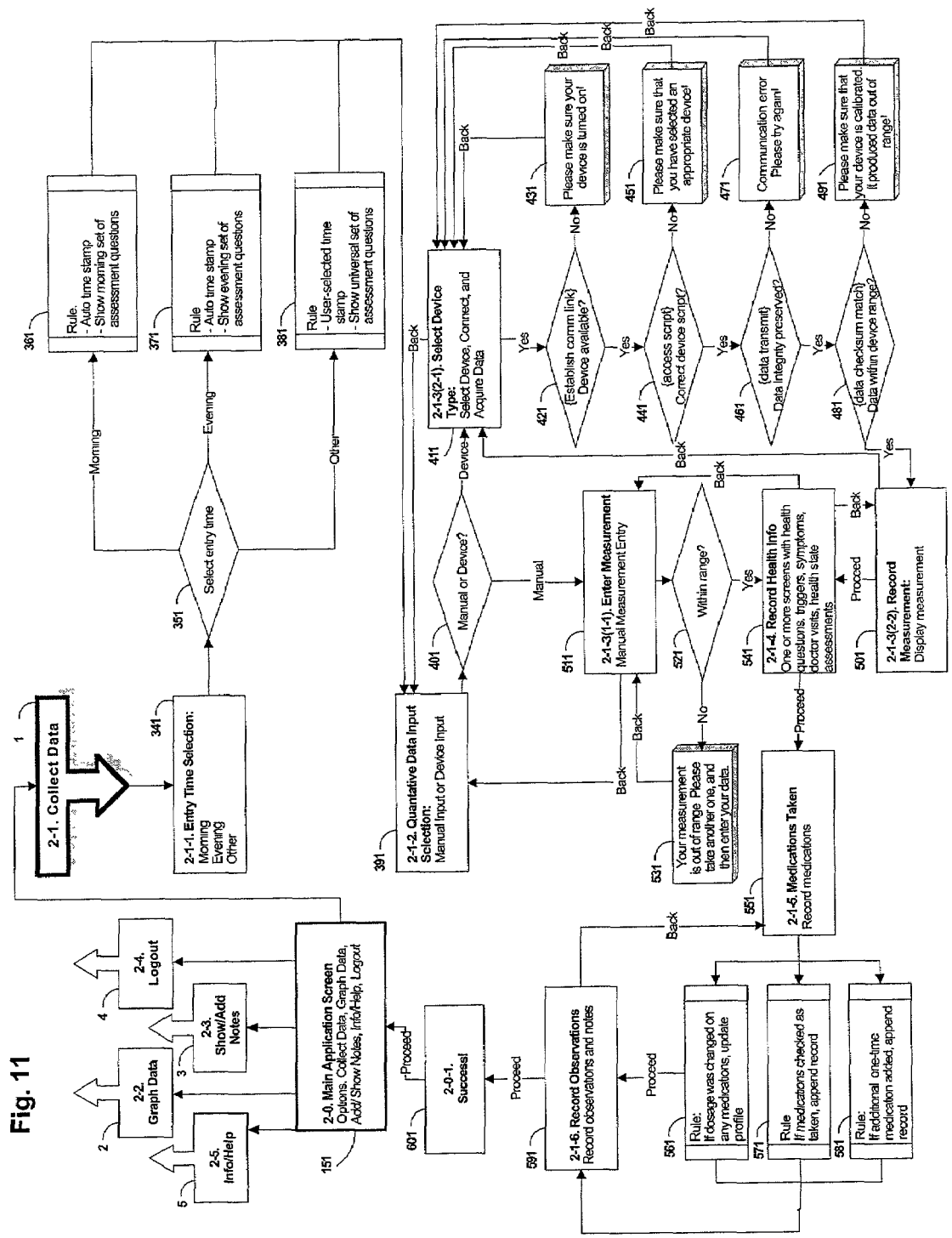
FIG. 11 is a schematic diagram showing a data collection aspect of the client shown in FIG. 10.

In FIG. 11, reference 1 indicates the beginning of the data collection function. The time of the entry is determined in step 341, and the particular assessment questions to be presented to the user are determined in steps 351, 361, 371, and 381. In step 391, it is determined whether the input will be from a person (i.e., manual input) or from a medical device. If the input is from a medical device, then processing is diverted at step 401 to step 411. If the input is manual, then processing is diverted to step 511.

Figure 16:
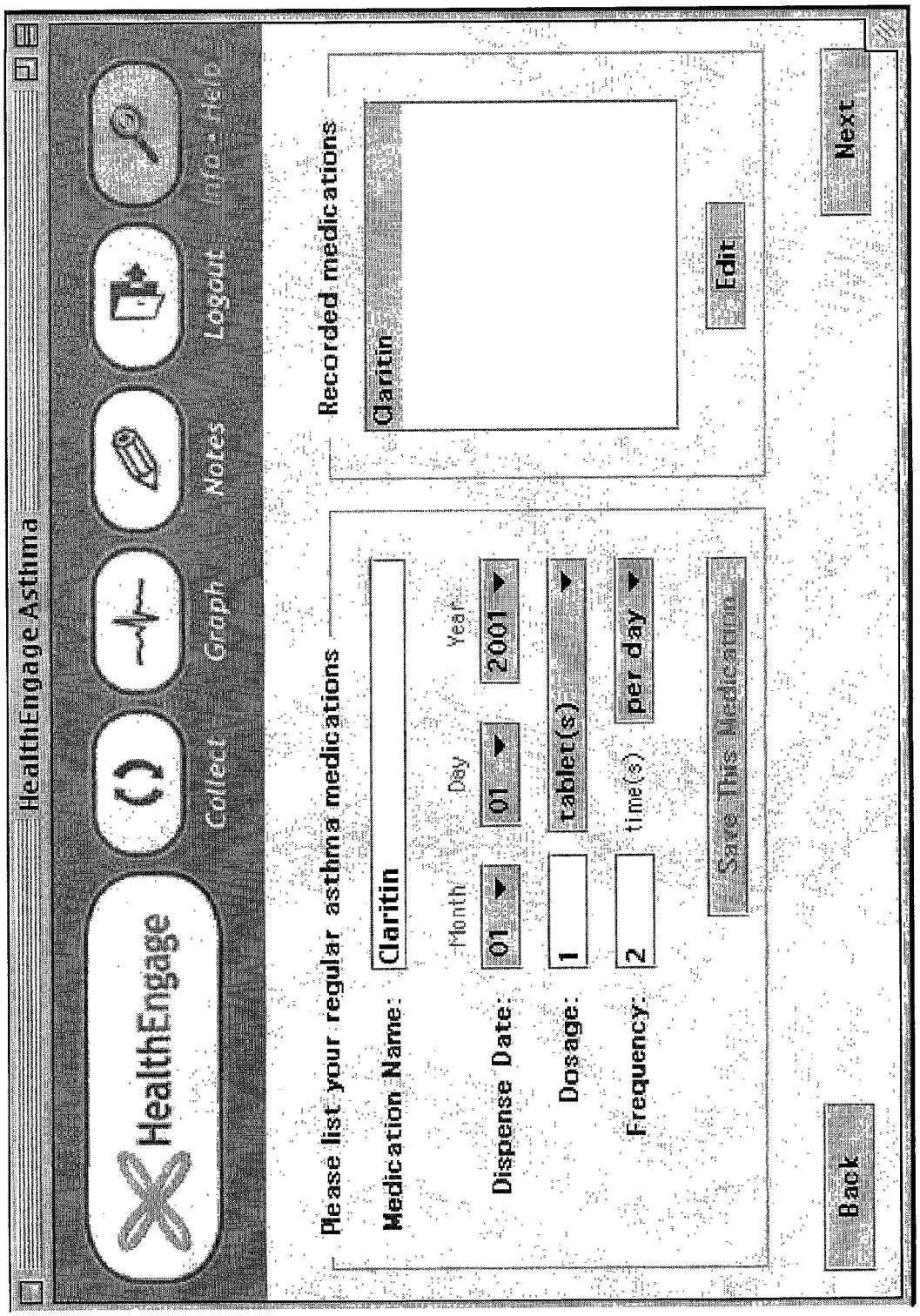
FIG. 16 shows an exemplary embodiment of a user interface screen.
Figure 17:
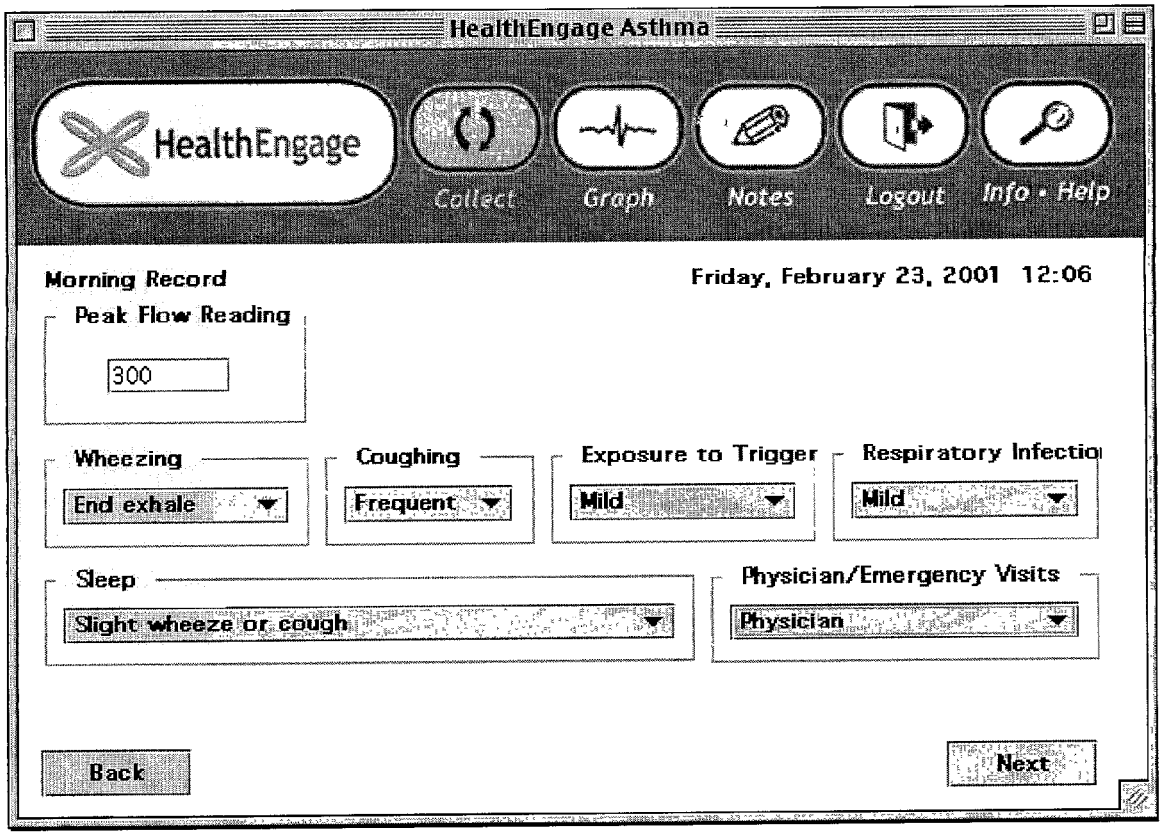
FIG. 17 shows another exemplary interface screen.

Assuming for the moment that the input is from a medical device, then the selection of the device, the connection to the device, and the acquisition of data is handled by the processing shown in steps 421, 431, 441, 451, 461, 471, 481, and 491. Afterwards, the measurement is displayed in step 501. Proceeding from step 501, processing continues with step 541, in which one or more screens with health related questions are presented. Medications information is obtained in step 551, (see FIG. 16) and it is determined whether the medication dosage was changed (step 561), whether the expected medications were taken (step 571), and whether additional one time medications were taken (step 581). These and other observations (see FIG. 17) may be recorded in step 591, and, once a successful indication is received, processing returns to main screen 151.

Assuming for the moment that the input was from a manual source, then processing from step 401 continues to step 511. Screens are presented so that the user can enter the measurement, and it is determined whether the entered measurements are within an appropriate range at step 521. If not, the user is invited to take another measurement and to enter the data in step 531. If the measurements are appropriate, then processing continues with step 541 and proceeds onward from that as described above.

Figure 12:
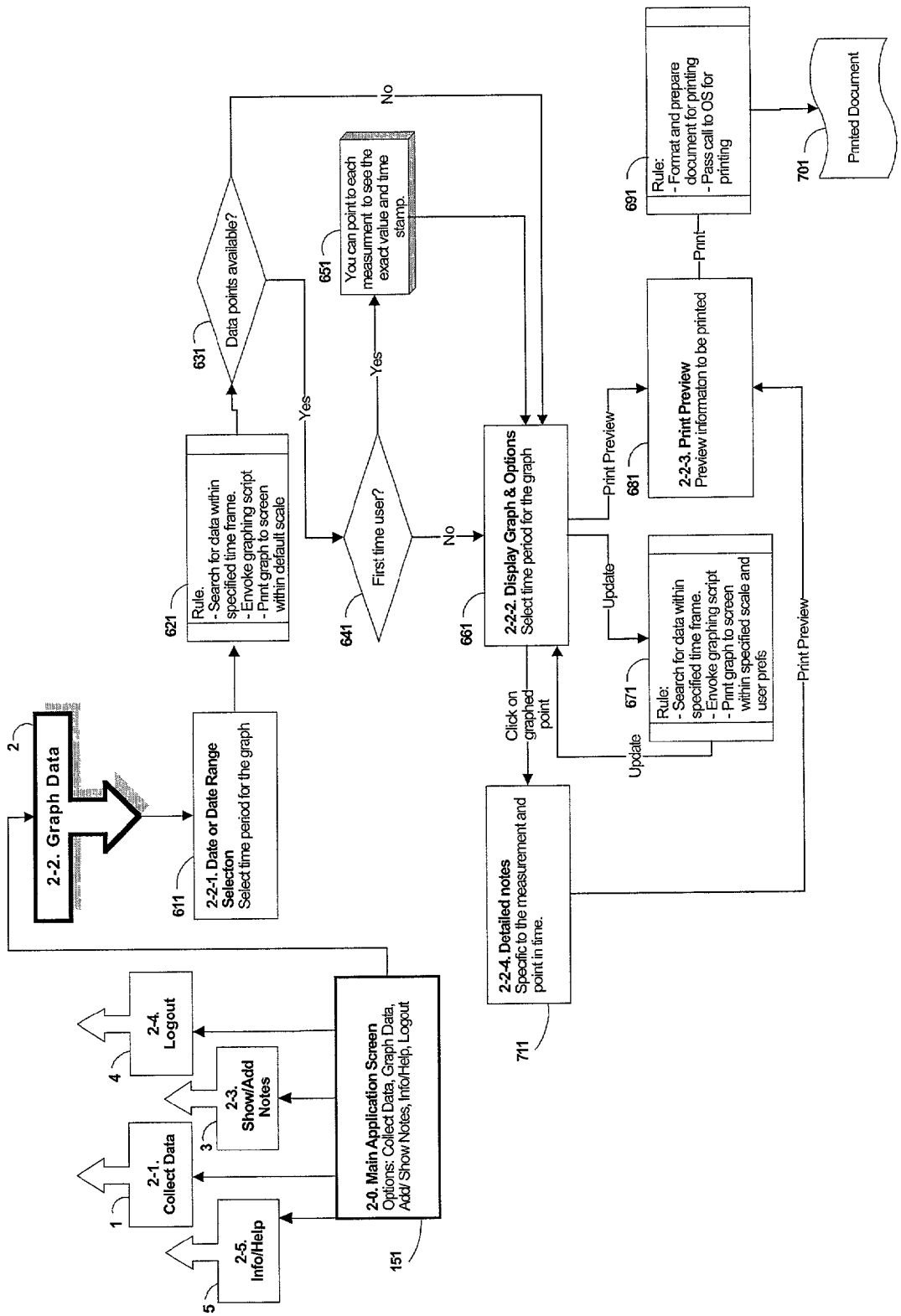
FIG. 12 is a schematic diagram showing a data graphing aspect of the client shown in FIG. 10.

FIG. 12 shows the data graphing function from the main application screen 151. In FIG. 12, reference 2 indicates the beginning of the data graphing function. Reference 611 indicates a step in which the user selects the date or Date range for graphing. Subject top the rule indicated in step 61, it is determined in step 631 whether data points are available for the graphing operation. If no points are available, the user is invited to select the time for the graphing step 661. If data points are available, and the user is a first-time user (as determined in step 641), then it is mentioned that the user can see the exact value and timestamp of a given measurement by pointing to the data point. Graphical display and printing functions are handled as shown in steps 671, 681, 691, and 711. Depending on what the user's requirements are, a printing document 701 may be generated.

Figure 13:
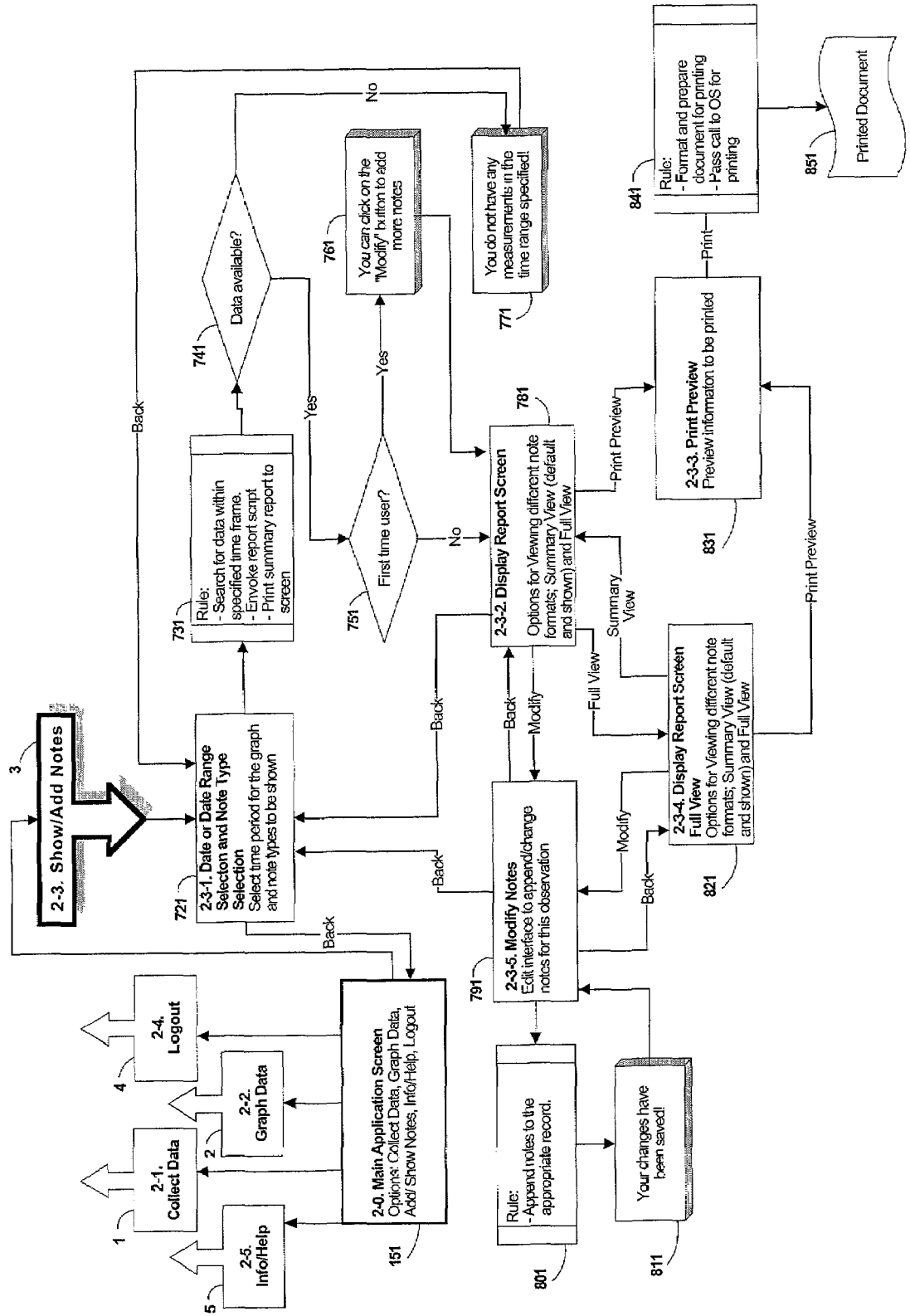
FIG. 13 is a schematic diagram showing and add/show notes aspect.

It will be recalled that, in FIG. 11, the recordation of observations and notes took place in step 591. FIG. 13 shows a function for displaying these notes, or for adding more notes. In particular, in FIG. 13, reference 3 shows the beginning of the function for showing or adding notes.

In step 721, the selection of the date or date range is performed. In accordance with the rule shown in step 731, is determined in step 741 whether such data is available. If not, processing continues to step 771 in which the user is informed that no measurements in the time range are available, and processing continues from there to step 721. If data is available, then, if the user is a first-time user is mentioned that the modify button can be activated to add more notes (steps 751 and 761). If the user is not a first-time user, then processing simply continues to the display reports screen 781. The selection of the particular format for displaying the notes, and the processing for modifying notes or appending notes is handled in a self-explanatory manner as shown in steps 791, 801, 811, 821, 831, 841, and 851.

Figure 14:
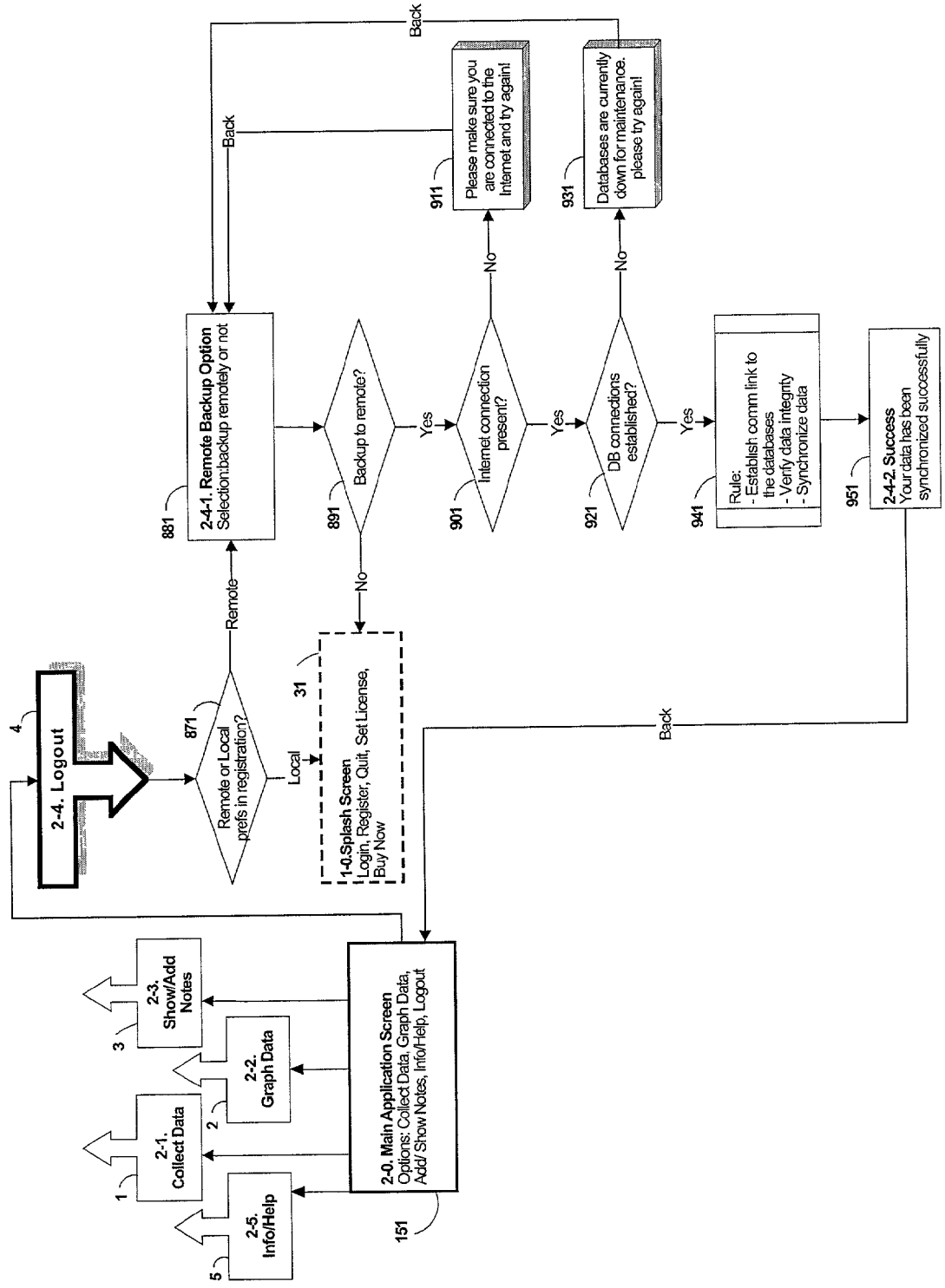
FIG. 14 a log out aspect.

FIG. 14 shows the operations to be completed upon the selection of a logout function 4. These functions are shown, in a self-explanatory manner, in steps 881, 891, 901, 911, 921, 931, 941, and 951.

Figure 15:
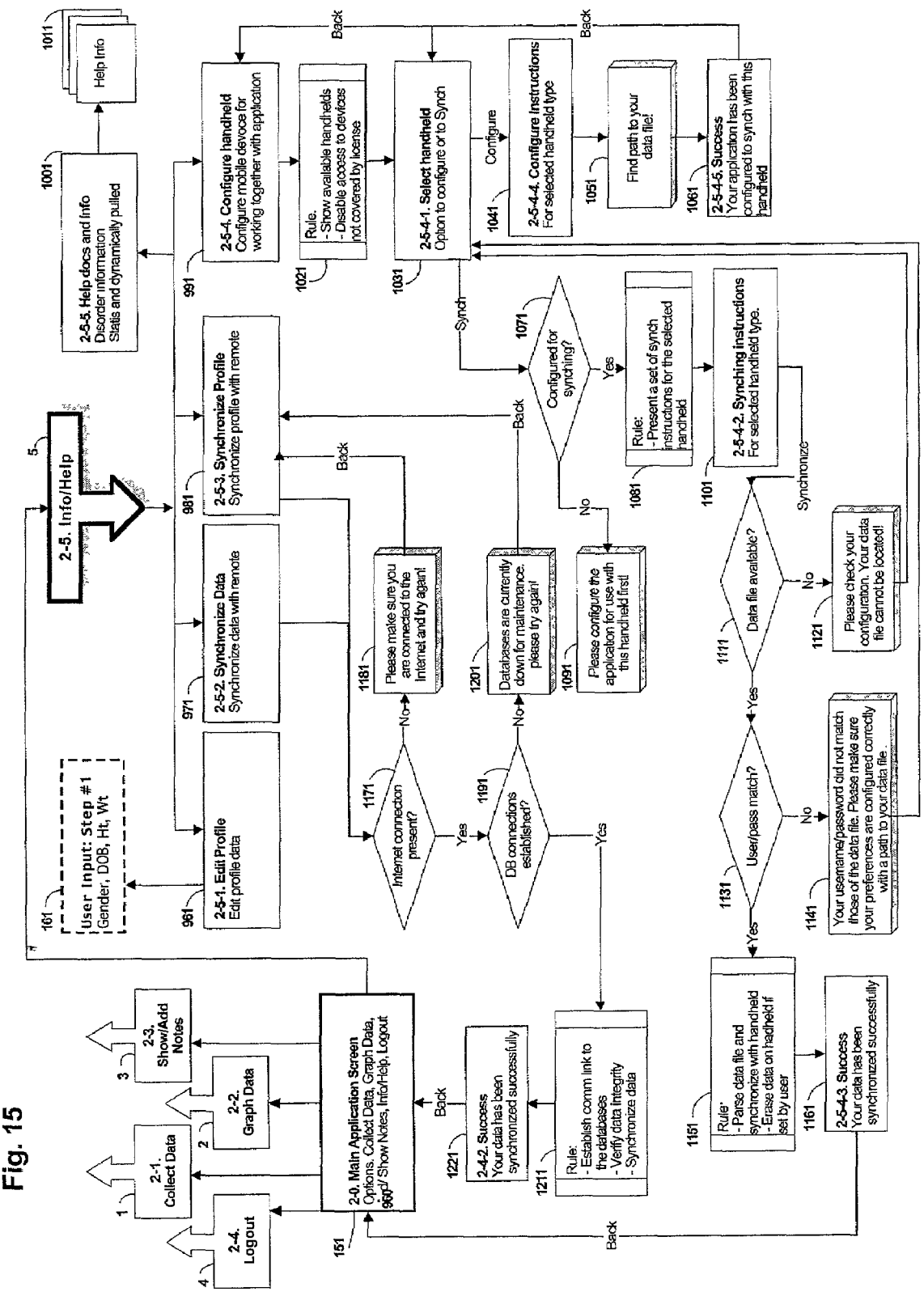
FIG. 15 a help/info aspect of the client shown in FIG. 10.

FIG. 15 shows the operations that may be performed upon the selection of an info/help function 5. When this function is invoked, a variety of operations may be undertaken. For example, at reference 961 there is shown an operation for the editing of profile data to change, e.g., the items shown in reference 161. At reference 971 there is shown an operation for synchronizing data and at reference 981 an operation for synchronizing profile information. Both of these operations carry out the logic shown in steps 1171, 1181, 1191, 1201, 1211, and 1221. That is to say, data from a remote source is synchronized with data in a database to which the data attention has access.

Another operation that may be undertaken is the configuration of a particular device, such as a handheld computing device or other similar remote device. This operation is shown at reference 991. The detailed processing steps, which may culminate in the synchronization of data held in the device and the data controlled by the data engine, are shown in steps 1021, 1031, 1041, 1051, 1061, 1071, 1081, 1091, 1101, 1111, 1121, 1131, 1141, 1151, and 1161.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention as defined in the following claims.

What is claimed is:

1. A clinical trial data management server method, comprising: receiving, at a server, a user profile provided by a client;
   based on said user profile, indicating to said client one or more matching clinical trials;
   receiving a clinical trail selection from said client;
   providing to said client a selected clinical trial module, indicated by said clinical trial selection and corresponding to a selected one of said matching clinical trials, said module being adapted to obtain clinical trial data including a respective data observation;
   receiving, at said server, said respective data observation;
   storing said respective data observation in a database of data observations; and
   in response to a report request:
   retrieving selected ones of said data observations from said database in accordance with parameters in said report request to provide a plurality of observations; and
   producing a report based on said plurality of retrieved observations, and
   wherein:
   said server includes a data engine;
   said server comprises a plurality of modules, including said selected clinical trial module, a health data management module, and a clinical trials management module;
   said health data management module comprises data analysis algorithms used by said data engine to analyze said clinical trial data; and
   said clinical trials management module:
   selects said one or more matching clinical trials, based on said user profile;
   provides an approval of said clinical trial selection; and
   provides said selected clinical trial module.

2. The clinical trial data management server method as set forth in claim 1, wherein said clinical trial data is provided to said server by a data sampling device.

3. The clinical trial data management server method as set forth in claim 1, wherein said clinical trial data is provided to said server over the Internet.

4. The clinical trial data management server method as set forth in claim 1, wherein said clinical trial data is provided to said server by a general-purpose computing device having said clinical trial data manually inputted by a user.

5. The clinical trial data management server method as set forth in claim 4, wherein said general-purpose computing device is one of: a personal computer, a handheld computing device, and a telephone.

6. The clinical trial data management server method as set forth in claim 1, wherein said clinical trials management module performs said selecting of said one or more matching clinical trial by comparing said received user profile with clinical trial profiles stored in a clinical trials database.

7. The clinical trial data management server method as set forth in claim 1, wherein said health data management module comprises data analysis algorithms and is adapted to accept data for one or more of: cardiology data, diabetes data, allergy data, and immunology data.

8. The clinical trial data management server method as set forth in claim 1, wherein said health data management module is adapted to send analyzed data to said client, said analyzed data comprising one or more of: a data display, complex data charting, and trend identification.

9. The clinical trial data management server method as set forth in claim 8, wherein said complex data charting comprises mathematical EKG pattern analysis.

10. The clinical trial data management server method as set forth in claim 8, wherein said trend identification is based on a plurality of said data observations form a plurality of different medical devices.

* * * * *